United States Patent
Ahrens et al.

(10) Patent No.: US 9,782,529 B2
(45) Date of Patent: Oct. 10, 2017

(54) EXTRACORPOREAL BLOOD TREATMENT DEVICE AND COLLECTING CONTAINER THEREOF

(71) Applicant: B. BRAUN AVITUM AG, Melsungen (DE)

(72) Inventors: Joern Ahrens, Baunatal (DE); Francesco Benatti, Mirandola (IT); Peter Pózna, Budapest (HU)

(73) Assignee: B. BRAUN AVITUM AG, Melsungen (DE)

( * ) Notice: Subject to any disclaimer, the term of this patent is extended or adjusted under 35 U.S.C. 154(b) by 61 days.

(21) Appl. No.: 14/922,580

(22) Filed: Oct. 26, 2015

(65) Prior Publication Data

US 2016/0129173 A1    May 12, 2016

(30) Foreign Application Priority Data

Nov. 10, 2014  (EP) .................................... 14192526

(51) Int. Cl.
*A61M 1/16* (2006.01)
*A61M 1/00* (2006.01)
*A61M 1/14* (2006.01)
*A61M 5/14* (2006.01)

(52) U.S. Cl.
CPC ........ *A61M 1/1621* (2014.02); *A61M 1/0019* (2013.01); *A61M 1/14* (2013.01); *A61M 5/14* (2013.01)

(58) Field of Classification Search
CPC .... A61M 1/0019; A61M 1/0209; A61M 1/14; A61M 1/1621; A61M 1/367; A61M 39/24; A61M 39/26; A61M 39/28
See application file for complete search history.

(56) References Cited

U.S. PATENT DOCUMENTS

| 5,954,951 A | 9/1999 | Nuccio |
| 6,558,340 B1 | 5/2003 | Traeger |
| 7,588,722 B2 * | 9/2009 | Chevallet ................ A61M 1/16 210/134 |

(Continued)

FOREIGN PATENT DOCUMENTS

| CN | 202 699 702 | 1/2013 |
| CN | 103857420 U | 6/2014 |

(Continued)

OTHER PUBLICATIONS

Japanese Exam Report for JP 2015-200562 dated Nov. 1, 2016.
(Continued)

*Primary Examiner* — Terry Cecil
(74) *Attorney, Agent, or Firm* — RatnerPrestia

(57) ABSTRACT

An extracorporeal blood treatment device is disclosed. The device includes a blood treatment unit connected to an extracorporeal blood circuit, a waste liquid discharge line for evacuating waste treatment liquid from the blood treatment unit, and a collecting container for collecting waste treatment liquid evacuated via the waste liquid discharge line. The collecting container is removably connected to the waste liquid discharge line via a one way valve. A collecting container for a device is also disclosed. The container includes a waste fluid input line, wherein a one way valve is arranged in the waste fluid input line.

15 Claims, 2 Drawing Sheets

(56) References Cited

U.S. PATENT DOCUMENTS

| | | | |
|---|---|---|---|
| 8,469,331 B2 * | 6/2013 | Burbank | A61M 1/1656 251/342 |
| 8,944,983 B2 * | 2/2015 | Nguyen | A61M 1/0209 494/2 |
| 2004/0267183 A1 | 12/2004 | Chevallet | |
| 2009/0182263 A1 | 7/2009 | Burbank | |
| 2014/0238912 A1 | 8/2014 | Vincent | |

FOREIGN PATENT DOCUMENTS

| | | |
|---|---|---|
| FR | 2539034 | 7/1984 |
| JP | H10-510747 | 10/1998 |
| JP | 2002-518105 | 6/2002 |
| JP | 2005319269 A | 11/2005 |
| JP | 2006-43315 | 2/2006 |
| JP | 2007-520248 | 7/2007 |
| JP | 2014-523313 | 9/2014 |
| WO | WO 2009/139878 | 11/2009 |
| WO | WO2013/003089 | 1/2013 |

OTHER PUBLICATIONS

European Exam Report for EP 14 192 526.3 dated Oct. 28, 2015.
Extended European Search Report for European Application No. 14192526.3-1651 dated Apr. 2, 2015.
Notice of Reasons for Refusal for Japanese Application No. 2015-200562, dated Mar. 24, 2017, including English translation, 6 pages.
First Chinese Office Action for Chinese Application No. 201510662709.2, dated Jun. 23, 2017, including English translation, 12 pages.

* cited by examiner

EXTRACORPOREAL BLOOD TREATMENT DEVICE AND COLLECTING CONTAINER THEREOF

CROSS REFERENCE TO RELATED APPLICATIONS

This application claims priority to European application EP 14192526.3 filed Nov. 10, 2014, the contents of such application being incorporated by reference herein.

FIELD OF THE INVENTION

The invention relates to a machine or device for extracorporeal blood treatment, the machine comprising a blood treatment unit, for example a filter device, connected to an extracorporeal blood circuit, a waste liquid discharge line for evacuating waste treatment liquid from the blood treatment unit and a collecting container for collecting waste treatment liquid evacuated via the waste liquid discharge line.

BACKGROUND OF THE INVENTION

Waste fluid that accumulates during an acute treatment, for example blood treatment, is usually collected in one or more waste bags located on a load cell of the machine. Measuring of volume of the waste fluid is a key feature to control fluid balance of the patient and a critical factor that requires monitoring and safety measures. The volume of the waste fluid contained in the waste bag is determined and supervised by the load cell. Waste bags that are filled during therapy are exchanged to empty ones to continue the therapy after a certain maximum filling volume is reached. In this event a user, for example a nurse or a patient, has to disconnect the bag from the machine. To avoid loss of fluid to the environment care has to be taken and usually clamps on both sides of the bag and the machine have to be closed.

To ease the life of the user, to make therapy more comfortable, to enable the user to use high flow rates and to have less disturbance during a running therapy due to a small number of bag changes, sufficient bag volume is required. However, handling of waste bags of large volume, with a weight of, for instance, 20 kg or even more is very inconvenient for the user.

To reduce volume and weight of the waste fluid containers it is known to use several waste fluid containers of smaller volume and therefore reduced weight instead of one waste fluid container. This enables the user to change the waste liquid container not too frequently, but with several containers of smaller volume at one time. As each container is connected to the same effluent line output, it cannot be achieved and guaranteed automatically, that each container is filled with same volume over time. This drawback may result in overloading one of the containers with the risk of destruction of some of them.

To avoid loss of waste fluid out of the system, especially out of the waste fluid container and the machine when disconnected, the use of standard Luer lock-connectors or manual clamps is state of the art. Current standard waste fluid containers usually comprise a fluid inlet tube provided with a clamp for closing the inlet tube and Luer lock-connector for connection with the machine. Additionally, they comprise a drain line also provided with a clamp for draining the container, if required.

DESCRIPTION OF THE RELATED ART

The U.S. Pat. No. 5,954,951 discloses a blood treatment circuit containing a blood treatment apparatus, the circuit comprising: a feedline for supplying fresh treatment liquid to the blood treatment apparatus; a waste liquid discharge line for evacuating waste liquid from the blood treatment apparatus; first measurement means for measuring an amount of liquid flowing through the waste liquid discharge line and for generating a signal indicative of a measured amount; a collecting container and an associated waste liquid withdrawal line for collecting a sample from the waste liquid discharge line, the withdrawal line having a first end connected to the waste liquid discharge line and a second end connected to the collecting container; and means for causing a metered flow of waste liquid into the collecting container at periodic intervals and as a function of volumetric flow through the waste liquid discharge line, to thereby collect a sample representative of all waste liquid discharged during at least a substantial portion of a treatment session, the metered flow causing means including second measurement means for measuring an amount of liquid flowing through the withdrawal line, obturation means for selectively restricting flow through the withdrawal line, and control means for selectively opening the obturation means each time the first measurement means has measured a first predetermined volume and for closing the obturation means each time the second measurement means has measured a second predetermined volume.

SUMMARY OF THE INVENTION

It is a significant drawback of known systems using several waste fluid containers that during therapy the waste fluid containers are not filled equally. In this case it is possible that one container or several containers are filled with more than the maximum volume of waste fluid. Further, if not every clamp disconnecting the containers from the waste fluid conduit is open for therapy, this may result in an overload or rupture of some of the other containers before the specified total volume of waste fluid is reached. Finally, usability of the system is reduced, if a user has to deal with several waste fluid containers having different waste fluid volumes, which makes it uncomfortable to monitor the situation.

It is an object of the invention to provide a machine or device for extracorporeal blood treatment with improved handling properties, wherein if several waste fluid containers are used the containers are filled equally and the risk of damage or rupture of one or more containers can be avoided.

To achieve this aim, according to aspects of the invention there is provided a device or an arrangement for acute treatment or extracorporeal blood treatment, said device or arrangement comprising a blood treatment unit, for example a filter device or a dialyzer, connected to an extracorporeal blood circuit, a waste liquid discharge line for evacuating waste treatment liquid from the blood treatment unit and a collecting container for collecting waste treatment liquid evacuated via the waste liquid discharge line, wherein the collecting container is removable connected to the waste liquid discharge line via a one way valve.

The term "one way valve" according to aspects of the invention defines check valves and non-return valves in general, for example a check valve, a double check valve, an in-line check valve, an angle check valve, a flap trap, a stop valve and similar valves. The one way valve preferably allows flow of waste fluid from the device into the collecting container and inhibits flow of waste fluid in the opposite direction. The one way valve in one embodiment is arranged on the side of the waste container and is disconnected together with the waste container from the device. Therefore, flow of waste fluid out of the container is automatically avoided, especially when the container is disconnected from the device. Further, there is no backflow of waste fluid into the device. Change of waste container is much easier for the user, as it is not required to close the waste container manually.

According to one embodiment of the invention the device comprises two or more collecting containers for collecting waste treatment liquid, which collecting containers are connected to the waste liquid discharge line in parallel. It is a significant advantage of the invention, that equal filling of each container can be achieved. The one way valves provided between each container and the device have each an identical flow resistance. Due to same flow resistances of the one way valves all waste container can be filled simultaneously and equally. After connection or disconnection of a waste container only one single clamp needs to be closed by the user, which is an improvement of usability to avoid loss of fluid into the environment. It should be understood that it is within the scope of the invention in case of two or more waste fluid collecting containers that one container, some containers or all containers may be designed and arranged according to the following description.

According to one embodiment the collecting container comprises a waste liquid input line, wherein the one way valve is arranged in the waste liquid input line. In one embodiment the one way valve is arranged at the distal end or the open end of the waste fluid input line, such that the latter is closable at its end. This avoids flow of waste fluid out of the collecting container if disconnected from the device.

According to another embodiment the collecting container comprises a waste liquid drain line for draining of waste treatment liquid out of the collecting container, which draining line preferably is provided with a clamp for temporary locking of the waste liquid drain line, preferably a Hanson-clamp.

According to another embodiment the one way valve is arranged in the waste liquid discharge line forming part of the device. A non-return valve arranged in the waste fluid discharge line of the device, especially on an outlet of said waste fluid discharge line, ensures simultaneous priming of each single of several containers and having no fluid outflow in case of only one line being connected to a container.

According to another embodiment the one way valve is arranged in the waste liquid input line. A non-return valve arranged on the collecting container side ensures having no outflow from the container when the latter is disconnected from the device. No clamps or similar devices need to be used and handled by a user, which eliminates the risk of opening only one container inlet in case of using several containers which cannot be recognized by the system without additional sensors.

According to another embodiment the waste liquid discharge line and the waste liquid input line are connected by a quick connecting means, preferably by a Luer-connector. This enables a quick and easy coupling and decoupling of the collecting container, for example when the maximum filling volume is reached.

According to another embodiment the one way valve is arranged in the quick connecting means. This ensures that almost no residual waste fluid contained in the waste line can enter the environment.

According to a further embodiment a clamp is arranged on a common part of the waste line. This ensures having no fluid outflow in case of removing the collecting container at container exchange.

According to aspects of the invention there is further provided a collecting container for a device, which container comprises a waste fluid input line, wherein a one way valve is arranged in the waste fluid input line. The collecting container according to one embodiment is a bag or a pouch. According to one embodiment the container is made at least in part or completely from a plastic material, for example of a plastic laminate. The container may comprise one or more sheets which are connected to each at their peripheral edges, for example by heat sealing.

According to one embodiment the collecting container is provided with a line in form of a waste fluid drain line, to be able to empty the containers content into a drain. Such a container may be used several times, which reduces waste.

According to a further embodiment at least one of the waste fluid input line and the waste fluid drain line is a flexible plastic hose. Especially the waste fluid discharge line may be closed by a clamp to avoid unintended loss of waste fluid therefrom. At least one of the waste fluid input line and the waste fluid drain line can be connected with the container in its sealing area, for example between the edges of the sheets forming the container. According to another embodiment the one way valve is arranged at the distal end of the waste fluid input line. Further, a quick connecting means, especially a Luer-lock connector, is arranged at the distal end of the waste fluid input line.

It is within the scope of invention to combine the aforementioned embodiments in any possible manner.

By the invention inter alia the following advantages may be achieved: Due to identical flow resistance of the one way valves in case of several containers each of them will be filled equally. With other words there will be an auto balancing effect of the filling volume of the containers connected to the waste fluid discharge line of the device. Further, there will be a risk reduction of container overloading due to missing volume balancing between multiple containers. Finally, there is only a reduced number of steps to be performed by a user to connect or disconnect a container with the device, which enhances usability.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
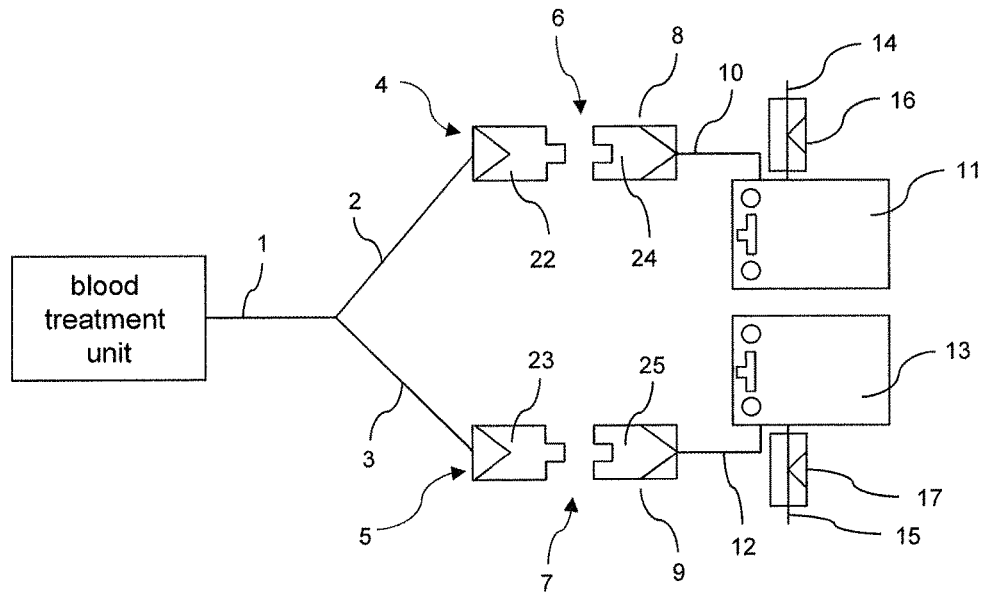
FIG. 1 shows in a schematic illustration part of a first example of a flow system of the invention.

FIG. 1 shows part of a waste fluid discharge line 1 of the device according to aspects of the invention. The waste fluid discharge line 1 is connected in a manner known per se with a blood treatment device of the device, for example a dialyzer. Such a dialyzer usually comprises a first compartment and a second compartment separated by a semipermeable membrane and connected respectively to a circuit for extracorporeal blood circulation and to a dialysis liquid circuit. The dialysis liquid circuit comprises a feed line, which is not shown in the drawings, for supply of fresh dialysis liquid, connected to an inlet of the second compartment of the dialyzer, and a discharge line connected to an outlet of the second compartment and to the waste fluid discharge line 1.

The waste fluid discharge line 1 is divided into a first waste fluid discharge branch 2 and a second waste fluid discharge branch 3. It should be noted that there may be additional branches. The first and second waste fluid discharge branches 2, 3 are provided with a male connecting member 4, 5 of a quick connecting means 6, 7. The quick connecting means 6, 7 also comprise female connecting members 8, 9. Female connecting member 8 is arranged at an input line 10 of a first waste fluid collecting container 11, while female connecting member 9 is arranged at an input line 12 of a second waste fluid collection container 13.

As can be seen from the diagram in FIG. 1, each male connecting member 4, 5 as well as each female connecting member 8, 9 is provided with a one way valve 22, 23, 24, 25. The one way valves 22, 23 are arranged in the first waste fluid discharge branch 2 and the second waste fluid discharge branch 3, respectively. The one way valves 24, 25 are arranged in the input line 10 and the input line 12, respectively. One way valves 22, 23 allow a flow from the waste fluid discharge line 1 into the input lines 10, 12 when the containers 11, 13 are connected. In case of disconnected containers 11, 13 the valves 22, 23 are closed and do not allow any waste fluid to leave the branches 2, 3. One way valves 24, 25 also allow a flow of waste fluid into the input lines 10, 12 but are closed for a flow in the opposite direction.

Figure 2:
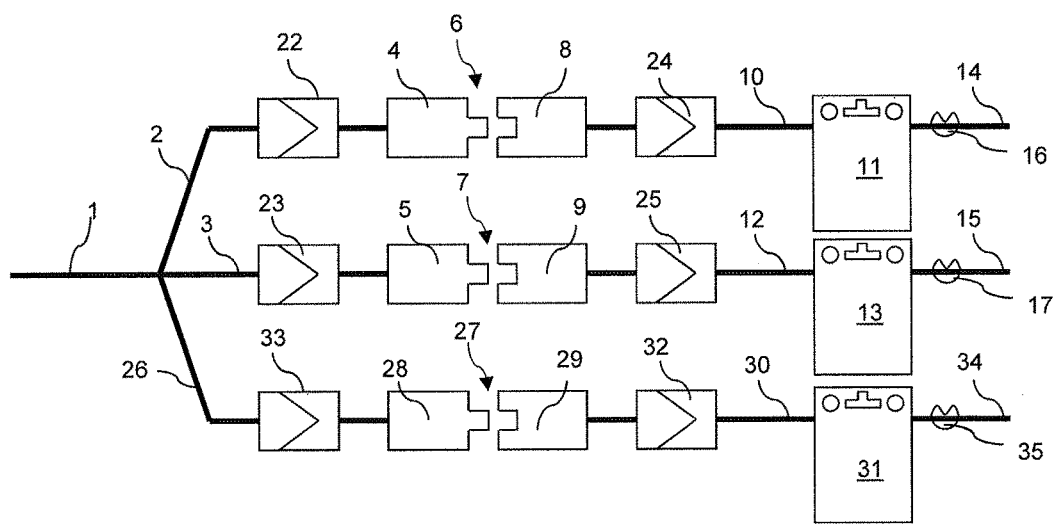
FIG. 2 shows in a schematic illustration part of a second example of a flow system of the invention and FIG. 3 shows part of a collecting container according to aspects of the invention.

FIG. 2 shows a second example of the flow system of the invention. The waste fluid discharge line 1 is connected in a manner known per se with a blood treatment device of the device, for example a dialyzer and is divided into a first waste fluid discharge branch 2, a second waste fluid discharge branch 3 and a third waste fluid discharge branch 26. Each waste fluid discharge branch 2, 3, 26 is provided with a quick connecting means 6, 7, 27, as already mentioned with regard to FIG. 1.

The connecting means 27 comprises a male connecting member 28 and a female connecting member 29. The latter is arranged at an input line 30 of a third waste fluid collecting container 31. Different than in the first embodiment the one way valves 24, 25, 32 are arranged in the input lines 10, 12, 30, respectively. One way valves 22, 23 and 33 are optional and if present arranged in the waste fluid discharge lines 2, 3, 26, respectively.

Each of the waste fluid collection containers 11, 13 comprises a waste fluid drain line 14, 15. The waste fluid drain line 14 is removably closed by a clamp 16, while the waste fluid drain line 15 is removable closed by a clamp 17.

Figure 3:
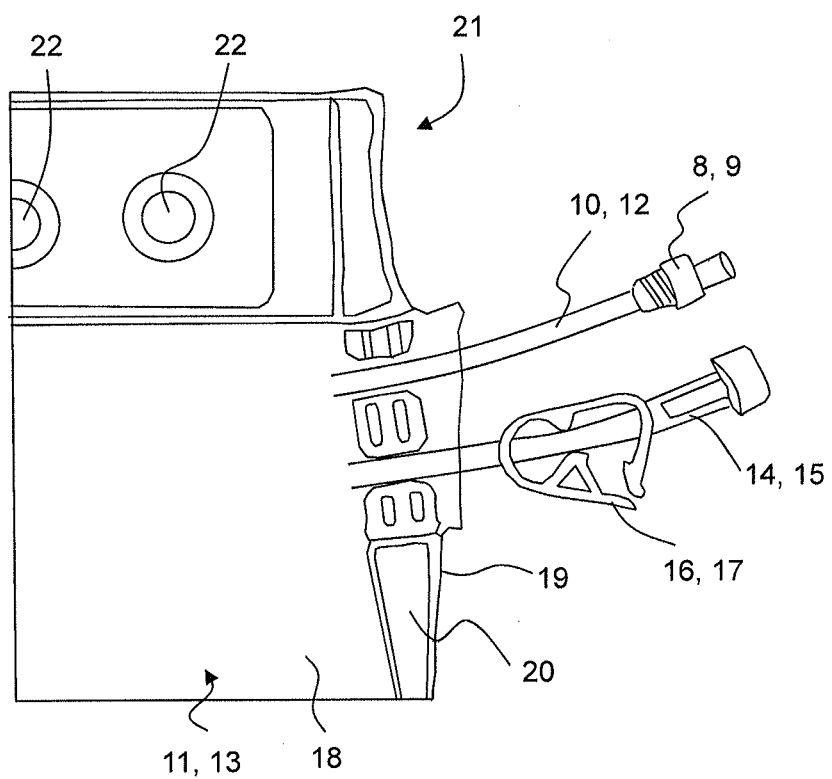

A detail of the containers 11, 13 is shown in FIG. 3. Each container 11, 13 is a bag or pouch formed by a front sheet 18 and a back sheet 19, which are sealed together at their peripheral edges by a sealing 20. An upper region 21 of each container 11, 13 is provided with fastening means 22 in form of holes, such that the containers during therapy can be hang up. The waste fluid input line 10, 12 as well as the waste fluid drain line 14, 15 are adhered to the container 11, 13 in the sealing area 20.

The invention claimed is:

1. An extracorporeal blood treatment device, comprising:
   a blood treatment unit connected to an extracorporeal blood circuit;
   a waste liquid discharge line connected to the blood treatment unit for evacuating waste treatment liquid from the blood treatment unit, the waste liquid discharge line having a plurality of waste discharge branches;
   a plurality of collecting containers, each of the plurality of collecting containers including a waste liquid input line connected to a respective waste discharge branch;
   a plurality of one way valves having the same flow resistance, the waste discharge branch or the waste liquid input line of each collecting container including a respective one way valve, wherein each of the plurality of collecting containers collects the waste treatment liquid evacuated via the waste liquid discharge line equally and simultaneously via the respective one way valve; and
   a plurality of quick connectors connecting each waste liquid input line to the respective waste discharge branch, each quick connector including:
   a first connecting member arranged on the respective waste discharge branch, and
   a second connecting member arranged on the respective waste liquid input line;
   wherein each of the plurality of collecting containers is removably connected to the waste liquid discharge line in parallel via the plurality of quick connectors and the plurality of one way valves.

2. The extracorporeal blood treatment device according to claim 1, wherein at least one of the plurality of one way valves is arranged in a respective waste liquid input line.

3. The extracorporeal blood treatment device according to claim 2, wherein at least one of the plurality of collecting containers further includes a waste liquid drain line for draining collected waste treatment liquid out of the at least one collecting container.

4. The extracorporeal blood treatment device according to claim 2, wherein the respective one way valve is arranged at an end of the waste liquid input line distal from the respective collecting container.

5. The extracorporeal blood treatment device according to claim 2, wherein the at least one of the plurality of one way valves and a quick connecting means are arranged at an end of a respective waste liquid input line distal from the respective collecting container.

6. The extracorporeal blood treatment device according to claim 2, wherein a quick connecting means is arranged at an end of a respective waste liquid input line distal from the respective collecting container.

7. The extracorporeal blood treatment device according to claim 1, wherein at least one of the plurality of collecting containers includes a waste liquid drain line for draining collected waste treatment liquid out of the at least one collecting container.

8. The extracorporeal blood treatment device according to claim 7, wherein the waste liquid drain line is provided with a clamp for temporary locking of the waste liquid drain line.

9. The extracorporeal blood treatment device according to claim 1, wherein at least one of the plurality of one way valves is arranged in a respective waste liquid discharge branch.

10. The extracorporeal blood treatment device according to claim 1, wherein at least one of the plurality of one way valves is arranged in a quick connecting means for a respective collecting container.

11. The extracorporeal blood treatment device according to claim 10, wherein the first connecting member includes the at least one of the plurality of one way valves.

12. The extracorporeal blood treatment device according to claim 10, wherein the second connecting member includes the at least one of the plurality of one way valves.

13. The extracorporeal blood treatment device according to claim 10, wherein:
the first connecting member includes a one way valve, and
the second connecting member includes a one way valve.

14. The extracorporeal blood treatment device according to claim 1, wherein the first connecting member is a male connecting element.

15. The extracorporeal blood treatment device according to claim 1, wherein the second connecting member is a female connecting element.

* * * * *